United States Patent [19]

Gittleman

[11] Patent Number: 5,580,247
[45] Date of Patent: Dec. 3, 1996

[54] CLAMPING MEANS FOR SECURING SURGICAL IMPLANT

[76] Inventor: Neal Gittleman, 15 Greenway Plz. #1D, Houston, Tex. 77046

[21] Appl. No.: 180,237

[22] Filed: Jan. 12, 1994

Related U.S. Application Data

[63] Continuation-in-part of Ser. No. 924,490, Aug. 4, 1992, Pat. No. 5,306,150.

[51] Int. Cl.$^6$ .................................................. A61C 8/00
[52] U.S. Cl. ............................................ 433/173; 433/176
[58] Field of Search .................................. 433/172, 173, 433/174, 175, 176; 623/16, 66

[56] References Cited

U.S. PATENT DOCUMENTS

| | | | |
|---|---|---|---|
| 3,720,959 | 3/1973 | Hahn | 623/16 |
| 3,908,269 | 9/1975 | Christenot et al. | |
| 4,062,119 | 12/1977 | Linkow et al. | 433/176 |
| 4,547,158 | 10/1985 | Roberts | 433/176 |
| 4,756,690 | 7/1988 | Roberts | 433/176 |
| 4,904,267 | 2/1990 | Bruce et al. | 623/16 X |
| 4,938,770 | 7/1990 | Frey et al. | 623/16 X |
| 5,035,712 | 7/1991 | Hoffman | 623/16 |
| 5,052,930 | 10/1991 | Lodde et al. | 433/176 X |

*Primary Examiner*—Nicholas D. Lucchesi
*Attorney, Agent, or Firm*—Ezra L. Schacht

[57] ABSTRACT

In today's dentistry, alternative approaches to the problem of mandibular reconstruction are important in restoring the mandible, which may have been lost through tumor resections, bone defects, pseudoarthosis or osteomyelitis.

Also for use in those situations in which the condyle or condylar process must be rebuilt or replaced, where portions of the condylar process such as the head, neck, and pterygoid fovea may have deteriorated through disease or from accidental injury. A condylar process arm may be fabricated as a substitute bearing surface for the defective natural condylar process.

3 Claims, 5 Drawing Sheets

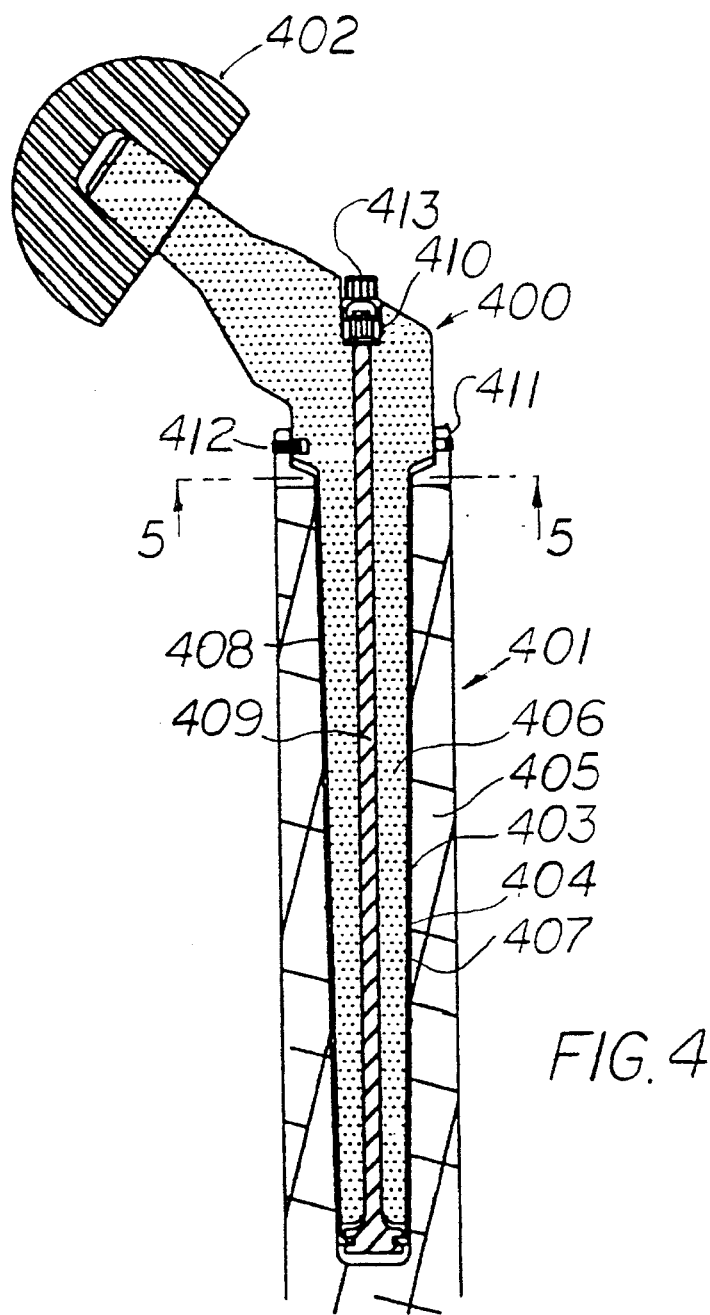
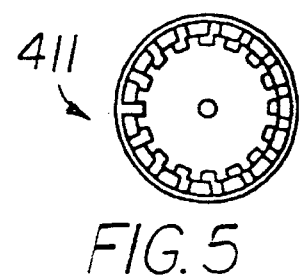
FIG. 4
FIG. 5

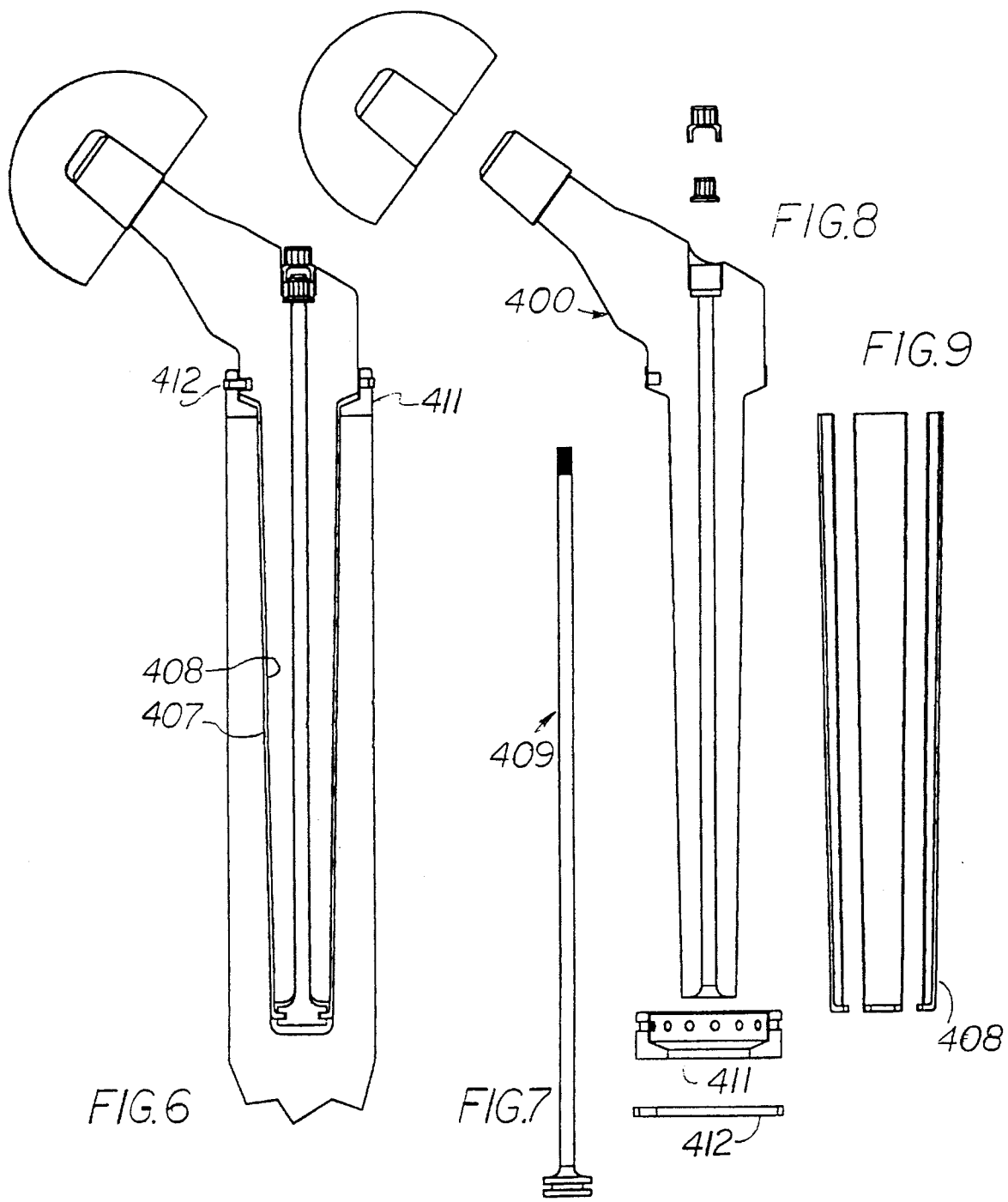

CLAMPING MEANS FOR SECURING SURGICAL IMPLANT

This is a continuation-in-part of application Ser. No. 07/924,490, filed on Sep. 4, 1992, now U.S. Pat. No. 5,306,150.

Disclosure Documents No. 316502 (Aug. 14, 1992) and No. 320959 (Dec. 3, 1992) are pertinent to this disclosure.

BACKGROUND OF THE INVENTION

A. EMBODIMENT FOR MANDIBULAR RECONSTRUCTION

An alternate embodiment of the dental ramus implant shown in copending application Ser. No. 07/924,490 is treated in this disclosure. It is an alternative approach to the problem of mandibular reconstruction. It is a novel apparatus and method for restoring the mandible, lost through tumor resections, bone defects, pseudoarthosis or osteomyelitis.

The biomechanical advantages of the ramus clamp of U.S. Pat. No. 5,306,150 can be combined with means to restore the mandible to overcome several of the problems which face the Cranofacial or Maxillofacial Surgeon. The present design overcomes the following problems associated with conventional techniques:

a. Fastening to the boney stump posteriorly becomes more predictable in the unilateral situation;

b. Bilateral or entire jaw replacement is more easily accomplished with a secure and straightforward procedure; and c. Dependency upon screws to anchor the posterior reconstruction is eliminated.

In the apparatus and method of the embodiment shown herein, no slots are made in the rami, but pre-designed clamps tightly grip the cortical surfaces and avoid the cancellous bone of the mandible, providing a secure hold without reducing the strength of the mandible.

B. EMBODIMENT FOR REPLACEMENT OF THE CONDYLAR PROCESS

In FIG. 2, a copy of FIG. 8 of Ser. No. 07/924,490 is shown as an alternate embodiment of the invention, for use in those situations in which the condyle or condylar process must be rebuilt or replaced. Portions of the condylar process 115, such as the head, neck, and pterygoid fovea may have deteriorated through disease or from accidental injury. A condylar process arm 120 may be fabricated as a substitute bearing surface for the defective natural condylar process.

As noted in U.S. Pat. No. 5,306,150, "it is also possible to apply this invention in the replacement of the condylar process and, of course, it may be applied in other defective condylar processes, elsewhere in the human anatomy, for which this construction is suitable."

The novelty of this invention resides primarily in the use of mechanically adjustable clamping apparatus and methods which do not weaken the cortical bone structure in order to securely mount a surgical clamp.

In the prior art, in the replacement of other defective condylar processes such as the condylar head of the femur, the prosthesis may be: forced into the femur; cemented in place; or screws may be driven into the bone.

The present invention avoids: crude pounding of the implant stem into the femoral canal, or equivalent canal in other bones, in order to achieve a press-fit of the implant; attempts to secure the shank of the implant within the internal bone canal with cements of uncertain reliability and indefinite life; and/or the use of wood screws, which rely upon the continuing elasticity of the bone to maintain solid contact between bone and prosthesis.

The present invention expands its clamps within the femoral canal in analogous fashion to the external clamping of the dental ramus clamp of U.S. Pat. No. 5,306,150. It uses a large bearing surface over which relatively low pressure can be maintained to secure and maintain solid bonding of prosthesis within the bone canal.

Other objects and advantages will become apparent in the following specification when considered in light of the drawings.

BRIEF DESCRIPTION OF THE DRAWINGS

FIG. 4 shows an axial cross section of the entire mechanism of a femoral implant in place in the femur and the artificial hip ball joint in the pelvis;

FIG. 5 shows a sectional view of the components of the lockring 411 and the vernier lockpin 412 which provide adjustment within one degree;

FIG. 6 shows an axial sectional view of the clamp mechanism with emphasis on the locking-ring mechanism;

FIG. 7 shows a profile view of the drawbar or stem 409;

FIG. 8 is an exploded view of the apparatus in FIGS. 4, 6; and

FIG. 9 is an axial sectional view of the tapered flexible clamps 408.

DESCRIPTION OF THE PREFERRED EMBODIMENTS

Figure 1:
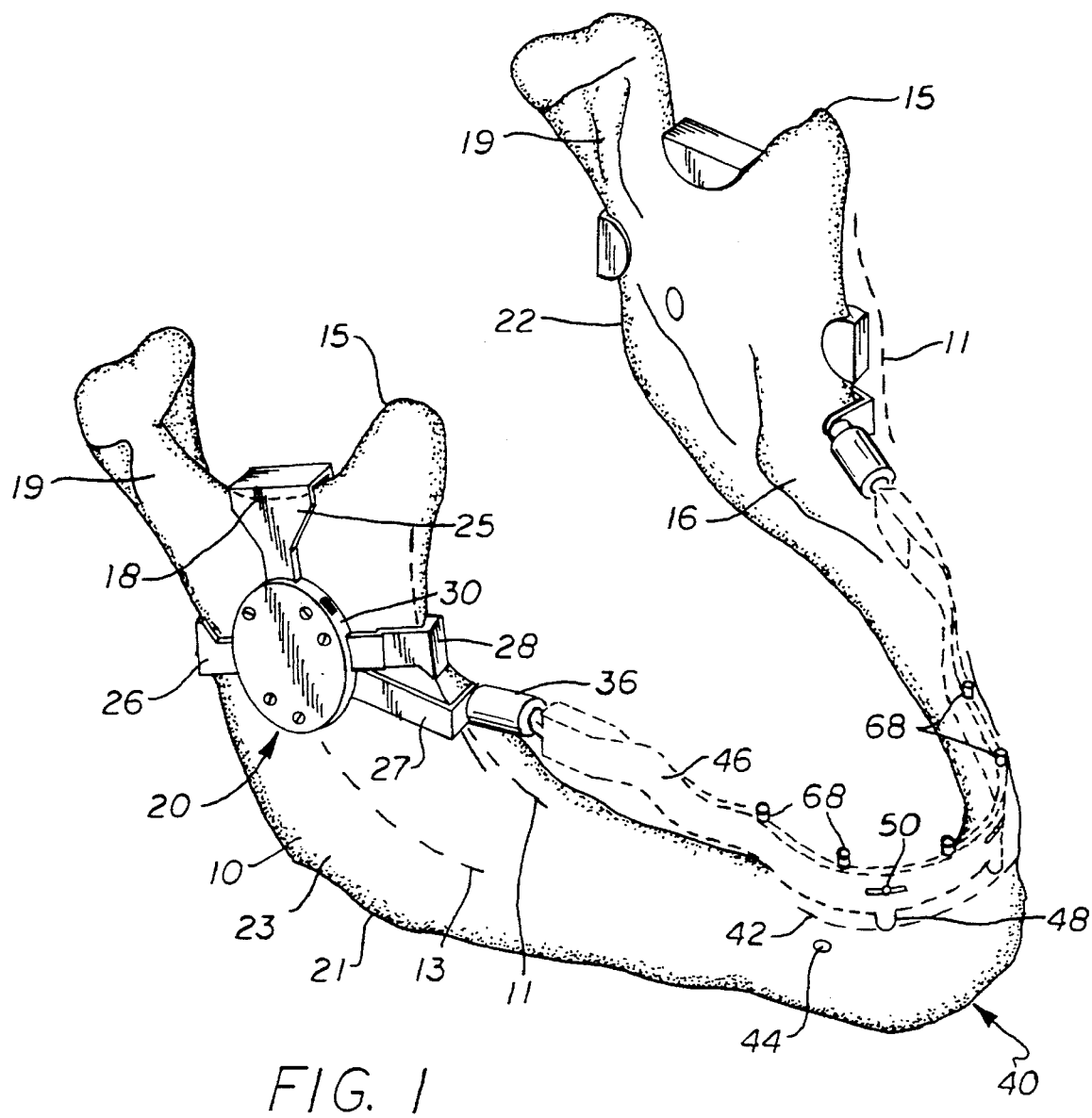
FIG. 1 is a copy of FIG. 1 from U.S. Pat. No. 5,306,150, with the anterior supporting framework 46 shown in dashed lines to indicate that it is not part of that invention.

Referring now to the drawings in detail, and in particular to FIG. 1. Therein illustrated is a ramus-clamp dental implant designated by the numeral 20. The ramus-clamp 20 is comprised of three adjustable arms secured to a non-rotable hub. The most superior component will henceforth be referred to as the superior securing arm 25. It is positioned over the sigmoid (or mandibular) notch 18. The posterior securing arm 26 is draped around the posterior aspect of the ramus. Both the superior securing arm 25 and the posterior securing arm 26 are extensions of the main body 30 of the ramus-clamp. Both securing arms lie in the same plane as the Interior articulating arm 27. The anterior articulating arm 27 ends in connecting means 36 to which may be secured the anterior supporting framework 46.

Figure 2:
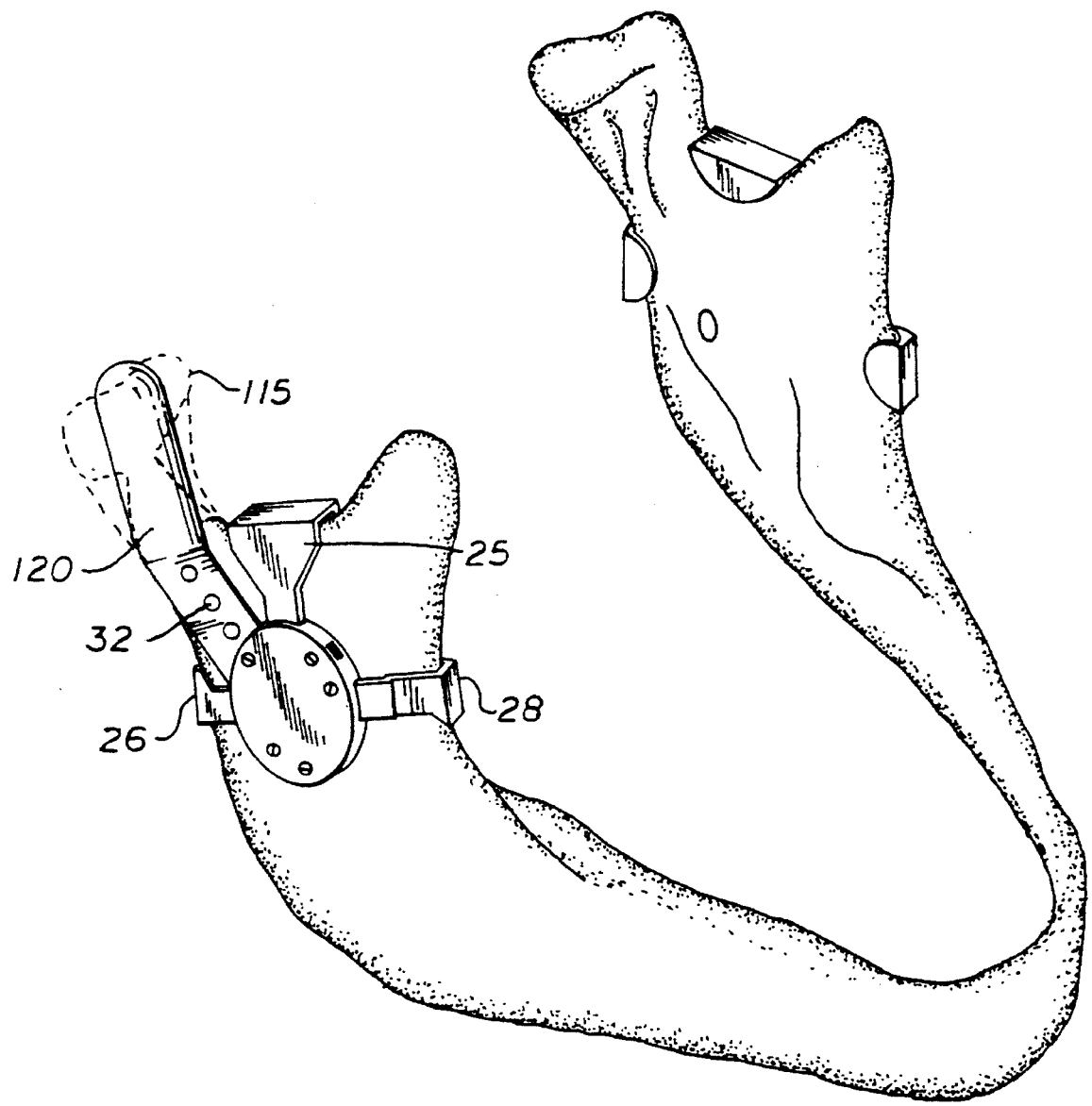
FIG. 2 shows the embodiment modified for replacement of the condyle or condylar process.

FIG. 2 shows the embodiment modified for replacement of the condyle or condylar process. As noted in the parent application, this is a generic apparatus for any locations in which the condyle or condylar process must be rebuilt or replaced. The numbers on the drawing are correlated with those used for the Preferred Embodiment. Portions of the condylar process 115, such as the head, neck, and pterygoid fovea may have deteriorated through disease or from accidental injury. A condylar process arm 120 may be fabricated as a substitute bearing surface for the defective natural condylar process. It may function in a manner similar to that of articulating arm 27 in FIG. 1.

Figure 3:
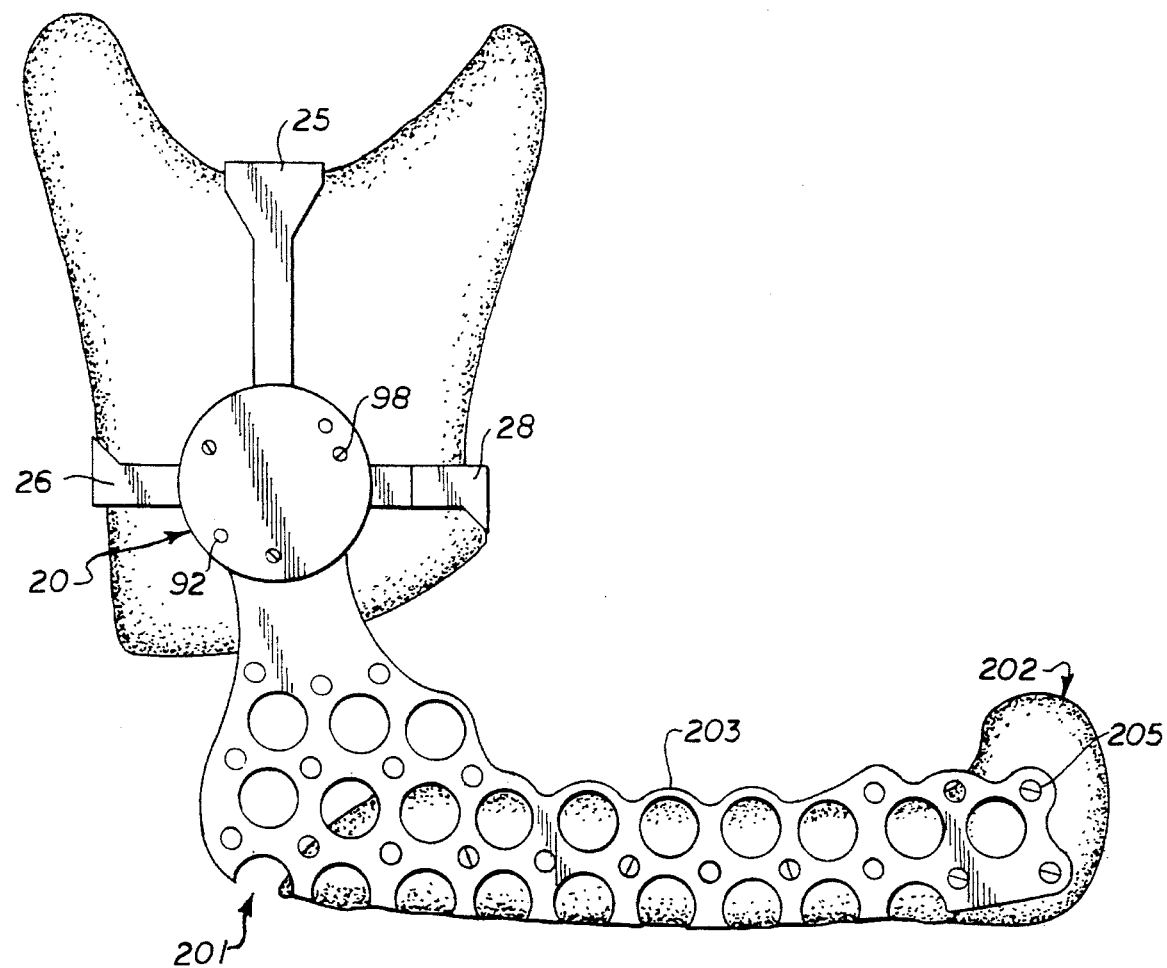
FIG. 3 shows the entire lower jaw replaced and supported by the dental ramus implant.

FIG. 3 shows the entire right lower jaw replaced and supported by the dental ramus implant. The anterior supporting framework 46 of FIG. 1, shown dashed to indicate that it was not part of the parent invention has now been replaced by an artificial mandible, or jawbone 201, which is one of the essential disclosures of this C.I.P. application. Part 202 may indicate: a portion of the mandible which is salvageable; a mechanical bond between mandible portion 201 and a mating mandible portion replacing the left half of the jawbone; or it may be nonexistant, in which case part 201 represents a complete jawbone fabricated to the dimensions of the original natural jawbone. Surface patterns such as dimples 203 may be incorporated for better bonding of the implant to the surrounding tissue. Other mechanical parts and methods may be used without departing from the spirit and intent of this invention.

It may thus be seen that both embodiments may be used for one patient, in a combined apparatus of FIGS. 1 and 3, should such an unfortunate complication arise.

FIG. 4 shows an axial cross section of the entire mechanism of a femoral implant 400 in place in the femur 401. The artificial hip ball joint 402, preferably a ceramic-surfaced casehardened zirconium ball is shown in its relative position in the pelvis. The wall 403 of the tapered tubular aperture, generally between the cortical and the cancellous bone 406 (replaced in this section by the stem of the prothesis) is bored with a state-of-the-art milling machine. Prior to the actual boring, CAT or MRI scans have established the critical dimensions of the cortical bone 405 and the cancellous bone 406. The cutting profile of the mill has been sized to remove as little of the cortical bone 405 as possible to conserve the natural strength of the femur 401 to avoid fractures in the event of a fall, and to provide maximum resistance of the interior cortical wall surface 407 against the action of expansion sleeve 408, as the drawbar (or stem) 409 is pulled upward and snugly seats the flexible tapered members 408 against the cortical bone interior wall 407.

The expansion sleeve (tapers) 408 has an oxidized coarse exterior and a smooth hardened interior. Stem 409 is of nitro-oxy diffusion hardened all over for wear resistance with ductility and endurance.

METHOD OF INSTALLATION AND REMOVAL

Installation:

1. Bore Femur 401 to proper diameter and depth;
2. Position assembly 400 to desired depth and rotation;
3. Tighten nut 410 to pull stem 409 down into femur 401;
4. Rotate support ring 411 to engage top of femur 401; and
5. Engage lockring 412 in aligned holes.

Removal:

1. Remove top cover 413;
2. Remove pull-rod nut 410;
3. Install extractor into top cover thread;
4. Rotate extractor to disengage tapers 406; and
5. Remove assembly 400 from femur 401.

A femoral structure may be strong but the canal may not be straight, requiring that portions of the reamed tubular canal depart from the entry centerline. With this apparatus and method, using a short-length milling cutter, such curved paths can be negotiated to preserve the maximum strength of the cortical bone 405.

It may also be necessary to anticipate and prevent cracking of the bone when the cortical femoral bone is relatively thin. One of the advantages of this invention is that it reduces the pressure against any small area of bone by spreading the securing force over a broad area, an effective method of assuring that no looseness will develop between the prothesis and the femur. There are reports that this looseness and the resultant feeling of insecurity and unsteadiness can make patients reluctant to attempt walking. It is an object of this invention to eliminate this possibility by the improved method and apparatus disclosed.

Virtually all mechanical connecting devices shown are solely illustrative examples appropriate for the need. Other variations will occur to those skilled in these mechanical arts, the application of which do not affect the claims of this invention.

What is claimed is:

1. A clamp securable non-invasively to the ramus portion of the human mandible, at least the proximal portion of the mandible having deteriorated to a condition requiring replacement by an artificial mandible portion, the clamp having means for engagement with clampable surfaces of said ramus portion, the clamp comprising:

a generally thin central hub, the hub adapted to be positioned appropriately on said ramus portion; radiating from said hub, (1) two fixed securing arms, comprising a superior securing arm and a posterior securing arm, (2) an anterior artificial articulating arm, (3) an adjustable anterior securing arm; said hub further comprising, (a) means for securing said superior securing arm to a clampable surface of said ramus portion, (b) means for securing said posterior securing and within the posterior border of said ramus portion, said anterior articulating arm further comprising a downwardly curving portion having means for simulating the dimensional curvature of at least a portion of the human mandible.

2. A clamp as recited in claim 1, said clamp further comprising an artificial jawbone portion, said jawbone portion having means for rotatable engagement with said clamp.

3. A method of non-bone-invasively installing a clamp securable to the ramus portion of the human mandible, wherein at least a proximal portion of said mandible has deteriorated to a condition requiring replacement by an artificial jawbone portion, said clamp comprising a superior securing arm, an anterior securing arm, a posterior securing and arm an anterior articulating arm having a downwardly curving portion having means for simulating the dimensional curvature of at least a portion of said human mandible and an artificial mandible portion, said method comprising:

(a) exposing said ramus portion by incising through the mucosa in the area of the external oblique ridge;

(b) exposing the ascending portion of said ramus portion from the retromolar region superiorly to the coronoid tip;

(c) dissecting posteriorly to expose the sigmoid notch of said ramus portion and uncovering the lateral aspect of the ramus portion while exposing the angle of said mandible and its inferior border;

(d) placing both said superior and said posterior securing arms onto said sigmoid notch and posterior border respectively;

(e) seating said clamp into position and locking said clamp in place, (f) securing said artificial mandible portion in place.

\* \* \* \* \*